(12) United States Patent
Feldmann et al.

(10) Patent No.: US 8,683,844 B2
(45) Date of Patent: Apr. 1, 2014

(54) SENSOR MONITORING METHODS AND SYSTEMS

(75) Inventors: Scott T Feldmann, South Lyon, MI (US); Janean E Kowalkowski, Northville, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 217 days.

(21) Appl. No.: 13/222,025

(22) Filed: Aug. 31, 2011

(65) Prior Publication Data

US 2013/0047702 A1    Feb. 28, 2013

(51) Int. Cl.
*G01D 18/00* (2006.01)
*F01N 11/00* (2006.01)

(52) U.S. Cl.
USPC .............................................. 73/1.06; 60/277

(58) Field of Classification Search
USPC .................................................. 73/1.02, 1.06
See application file for complete search history.

(56) References Cited

U.S. PATENT DOCUMENTS

| | | |
|---|---|---|
| 8,555,613 B2 | 10/2013 | Wang et al. |
| 2002/0185107 A1 | 12/2002 | Kubesh et al. |
| 2008/0147295 A1 * | 6/2008 | Sivasubramaniam et al. ............... 701/103 |

FOREIGN PATENT DOCUMENTS

| | | |
|---|---|---|
| DE | 102007042749 A1 | 3/2009 |
| JP | 2003172192 A | 6/2003 |

OTHER PUBLICATIONS

English Abstract of JP03277961A published Dec. 9, 1991; Title: Electrochemical Gas Sensor, Applicant: Matsushita Electric Works Ltd, 1 page.

\* cited by examiner

*Primary Examiner* — Daniel S Larkin
*Assistant Examiner* — Irving A Campbell
(74) *Attorney, Agent, or Firm* — Cantor Colburn LLP

(57) ABSTRACT

A method of monitoring a sensor of an exhaust system is provided. The method includes evaluating humidity of air entering the exhaust system; and monitoring operation of a sensor in the exhaust system based on the humidity.

14 Claims, 4 Drawing Sheets

SENSOR MONITORING METHODS AND SYSTEMS

FIELD OF THE INVENTION

Exemplary embodiments of the invention relate to methods, systems, and computer program products for monitoring sensors of an exhaust system.

BACKGROUND

Exhaust gas emitted from an internal combustion engine, particularly a diesel engine, is a heterogeneous mixture that contains gaseous emissions such as carbon monoxide ("CO"), unburned hydrocarbons ("HC") and oxides of nitrogen ("NOx") as well as condensed phase materials (liquids and solids) that constitute particulate matter. Catalyst compositions typically disposed on catalyst supports or substrates are provided in an engine exhaust system to convert certain, or all of these exhaust constituents into non-regulated exhaust gas components.

Sensors are provided in the engine exhaust system to measure the levels of the emissions. In particular, a NOx sensor can be disposed within the engine exhaust system to measure the NOx levels in the exhaust gas. The internal combustion engine is controlled based on the NOx sensor readings to reduce the level of NOx. Thus, proper operation of the engine is based on proper operation of the NOx sensor.

Accordingly, it is desirable to provide systems and methods for monitoring the functionality of the NOx sensors to ensure proper operation.

SUMMARY OF THE INVENTION

In one exemplary embodiment, a method of monitoring a sensor of an exhaust system is provided. The method includes evaluating humidity of air entering the exhaust system; and monitoring operation of a sensor in the exhaust system based on the humidity.

The above features and advantages and other features and advantages of the invention are readily apparent from the following detailed description of the invention when taken in connection with the accompanying drawings.

BRIEF DESCRIPTION OF THE DRAWINGS

Other objects, features, advantages and details appear, by way of example only, in the following detailed description of embodiments, the detailed description referring to the drawings in which.

DESCRIPTION OF THE EMBODIMENTS

Figure 1:
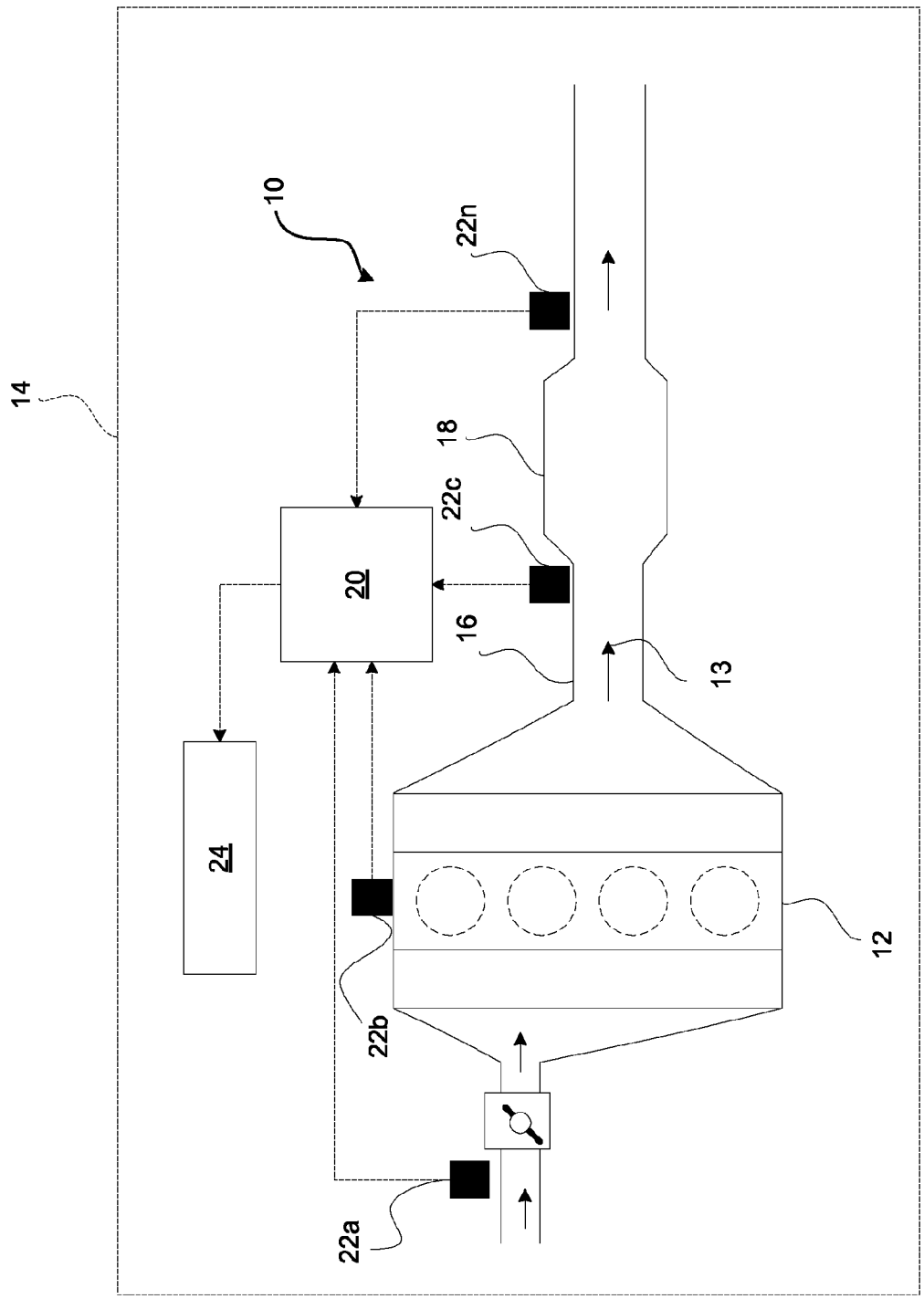
FIG. 1 is a schematic of a vehicle including an exhaust system in accordance with exemplary embodiments.

The following description is merely exemplary in nature and is not intended to limit the present disclosure, its application, or uses. It should be understood that throughout the drawings, corresponding reference numerals indicate like or corresponding parts and features. As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality.

Referring now to FIG. 1, exemplary embodiments are directed to an exhaust gas treatment system 10, for the reduction of regulated exhaust gas constituents of an internal combustion engine, such as an engine 12, of a vehicle 14. As can be appreciated, the engine 12 can be of any engine type including, but not limited to, a diesel engine, a gasoline direct injection engine, a homogeneous charge compression ignition engine, or other engine type.

The exhaust gas treatment system 10 generally includes one or more exhaust gas conduits 16, and one or more exhaust treatment devices 18. In various embodiments, the exhaust treatment devices 18 can include an oxidation catalyst device, a selective catalytic reduction device, a particulate filter, and/or other treatment device.

In FIG. 1, the exhaust gas conduit 16, which may comprise several segments, transports exhaust gas 13 from the engine 12 to the various exhaust treatment devices 18 of the exhaust gas treatment system 10. The exhaust treatment devices 18 operate to filter the exhaust gas 13 of emissions and particulate matter.

A control module 20 controls the engine 12 and/or one or more exhaust components based on sensed and/or or modeled data. The sensed data can be received from one or more sensors 22a-22n of the exhaust treatment system 10. In particular, at least one NOx sensor 22c senses the amount of NOx in the exhaust gas 13. As can be appreciated, multiple NOx sensors 22c can be disposed within the exhaust treatment system, for example upstream and/or downstream of the exhaust treatment devices 18.

In various embodiments, the control module 20 monitors the operation of the NOx sensor 22c and diagnoses the operation of the NOx sensor 22c based on a determination of the humidity of air within the exhaust treatment system 10. In various embodiments, the humidity can be determined based on one or more sensed inputs or measured directly from a sensor (e.g., via sensor 22a that measures the humidity in the intake air stream). The control module 20 can set a diagnostic code 24 based on the diagnosis. The control module 20 can further report the diagnostic code 24 according to various reporting methods, including, but not limited to, using in-vehicle communication reporting messages and/or off-vehicle reporting messages.

Figure 2:
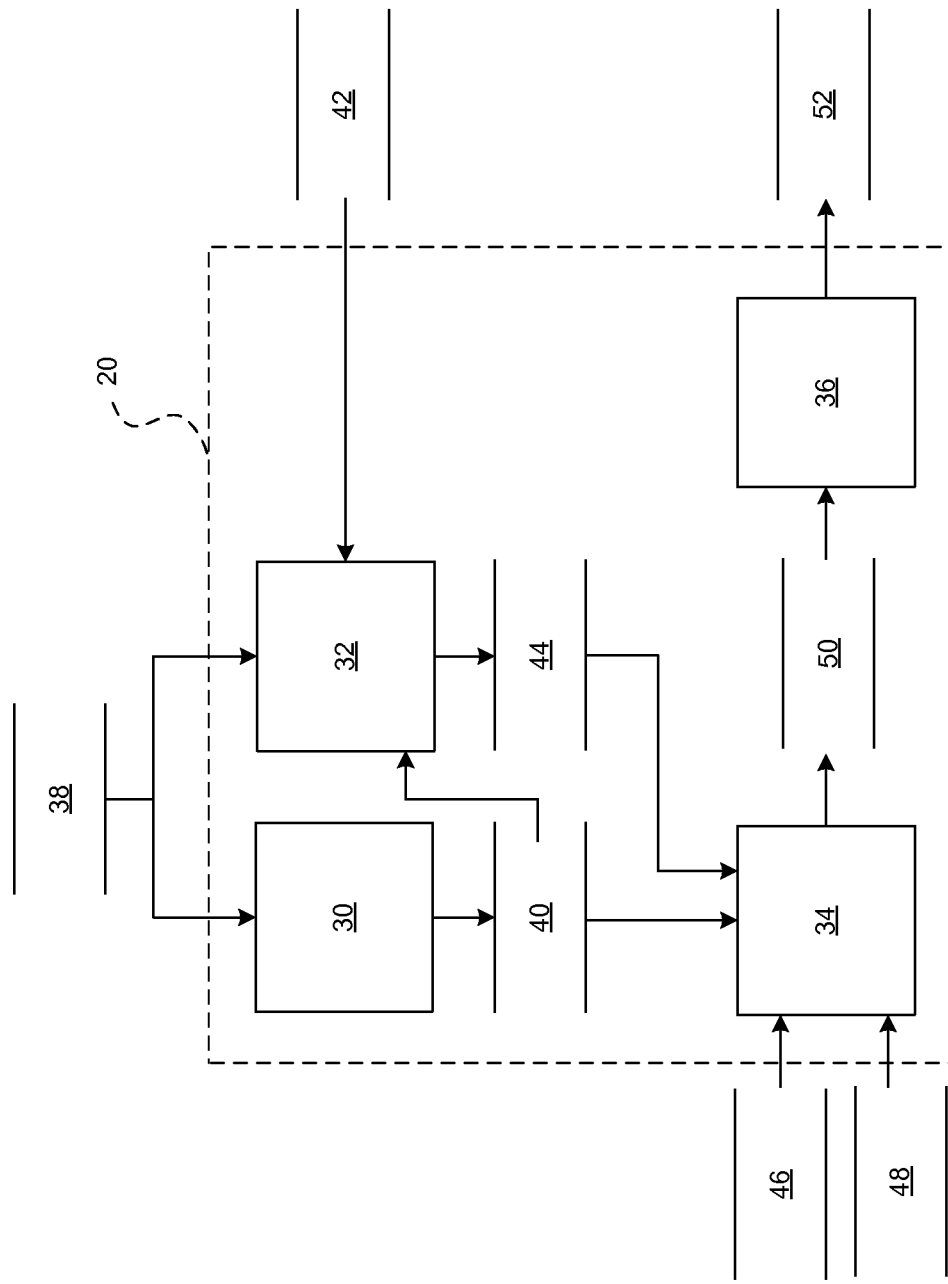
FIG. 2 is a dataflow diagram illustrating a sensor monitoring system of the exhaust system in accordance with exemplary embodiments.

Referring now to FIG. 2, a dataflow diagram illustrates various embodiments of a sensor monitoring system that may be embedded within the control module 20. Various embodiments of sensor monitoring systems according to the present disclosure may include any number of sub-modules embedded within the control module 20. As can be appreciated, the sub-modules shown in FIG. 2 may be combined and/or further partitioned to similarly monitor sensor operation of NOx sensors 22c (FIG. 1). Inputs to the system may be sensed from the engine 12 (FIG. 1) via sensors 22a-22n (FIG. 1), received from other control modules (not shown), and/or determined/modeled by other sub-modules (not shown) within the control module 20. In various embodiments, the control module 20 includes an enable module 30, a threshold determination module 32, an evaluation module 34, and a reporting module 36.

The enable module 30 receives as input the humidity data 38. The enable module 30 evaluates the humidity data 38 and enables the monitoring of the NOx sensor 22c based thereon. For example, if the humidity data 38 indicates that the humidity is within a range (e.g., less than a high threshold and greater than a low threshold), the enable module 30 enables the monitoring via an enable flag 40 (e.g., sets the enable flag 40 to enabled). In another example, if the humidity data 38 indicates that the humidity is outside of the range (e.g., greater than the high threshold, and less than the low threshold), the enable module 30 disables the monitoring via the enable flag 40 (e.g., sets the enable flag 40 to disabled).

The threshold determination module 32 receives as input the enable flag 40, the humidity data 38, and other engine data 42 (e.g., engine speed, fuel amounts, etc.). When the enable flag 40 indicates that the monitoring is enabled, the threshold determination module 32 determines a final threshold 44 using the inputs 38, 42. For example, the threshold determination module 32 determines a base threshold based on fuel and engine speed data. For example, the base threshold can be determined from a lookup table that is accessed by the engine speed and fuel. The threshold determination module 32 then determines a humidity correction factor based on the humidity data 38. For example, if the humidity is within a second range (e.g., less than a high threshold and greater than a low threshold), the humidity correction factor can be determined from a lookup table that is accessed by the humidity data 38. The threshold determination module 32 then applies the humidity correction factor to the base threshold to determine the final threshold 44.

The evaluation module 34 receives as input NOx sensor data 46, modeled NOx data 48, the enable flag 40, and the final threshold 44 and sets a pass/fail status 50 based thereon. For example, when the enable flag 40 indicates that the monitoring is enabled, the evaluation module 34 compares the NOx sensor data 46 with the modeled NOx data 48 to determine a difference. The evaluation module 34 then compares the difference with the final threshold 44 to determine if the NOx sensor 22c (FIG. 1) is operating as expected. If the NOx sensor 22c (FIG. 1) is operating as expected, the evaluation module 34 sets the pass/fail status 50 to PASS. If, however, the NOx sensor 22c (FIG. 1) is not operating as expected, the evaluation module 34 sets the pass/fail status 50 to FAIL.

The reporting module 36 receives as input the pass/fail status 50. Based on the pass/fail status 50, the reporting module 36 sets the value of the diagnostic code 24 associated with the NOx sensor 22c (FIG. 1) and reports the diagnostic code 24. In various embodiments, the diagnostic code 24 can be reported by generating a message on a serial data bus (not shown) of the vehicle 14 (FIG. 1), where the message can be transmitted to a remote location using a telematics system (not shown) of the vehicle 14 (FIG. 1) or can be retrieved by a technician tool (not shown) connected to the vehicle 14 (FIG. 1).

Figure 3:
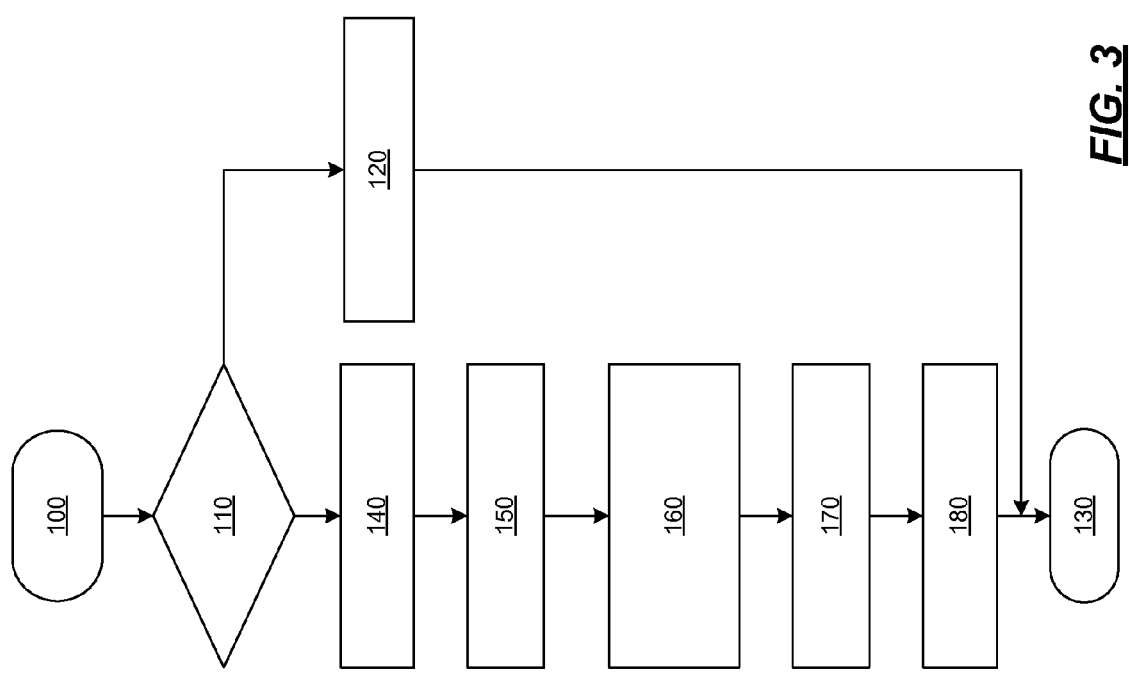
FIG. 3 is a flowchart illustrating a sensor monitoring method that may be performed by the exhaust system in accordance with exemplary embodiments.
Figure 4:
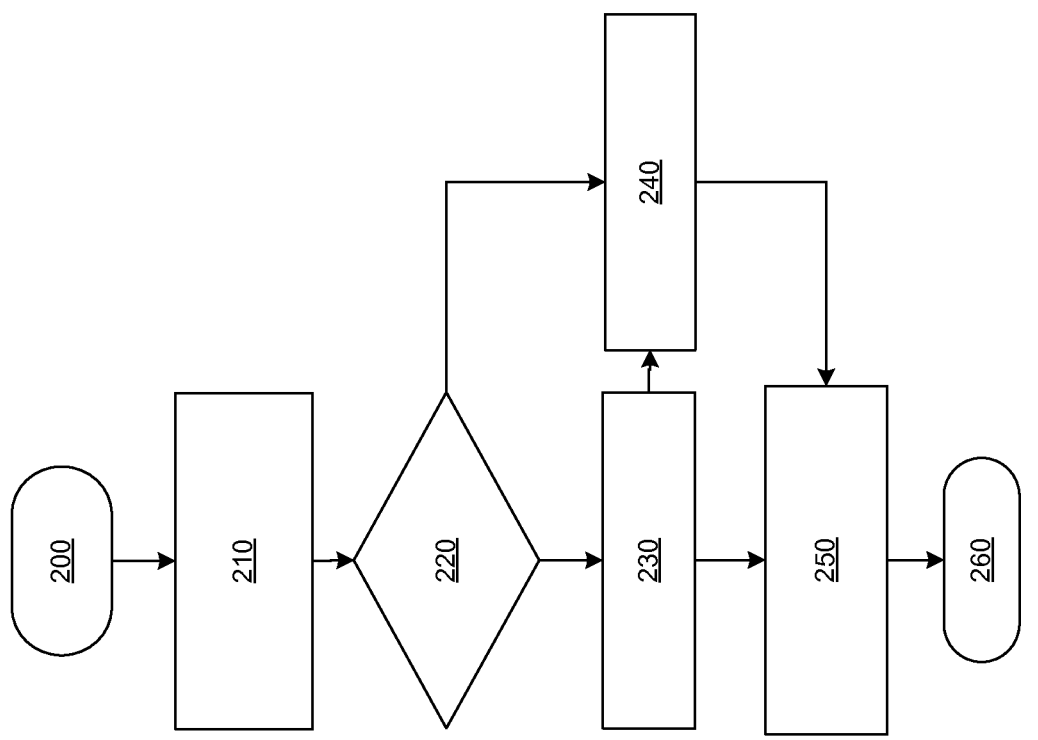
FIG. 4 is a flowchart illustrating a threshold determination method that may be performed by the exhaust system in accordance with exemplary embodiments.

Referring now to FIGS. 3 and 4, and with continued reference to FIGS. 1 and 2, a flowchart illustrates a sensor monitoring method that can be performed by the control module 20 of FIG. 1 in accordance with the present disclosure. As can be appreciated in light of the disclosure, the order of operation within the method is not limited to the sequential execution as illustrated in FIG. 3, but may be performed in one or more varying orders as applicable and in accordance with the present disclosure.

In various embodiments, the method can be scheduled to run based on predetermined events, and/or run continually during operation of the engine 12.

With reference now to FIG. 3, the method may begin at 100. The humidity data 38 is evaluated at 110. If the humidity is outside of the range at 110, the monitoring is disabled at 120 and the method may end at 130.

If, however, the humidity is within the range at 110, the monitoring of the NOx sensor 22c is enabled at 140. The final threshold 44 is determined at 150 (as shown in FIG. 4). The measured NOx data 46 is compared to the modeled NOx data 48 and the difference is compared to the final threshold 44 at 160. The pass/fail status 50 is set based on the comparison at 170 and the diagnostic code 24 is set and reported at 180. Thereafter, the method may end at 130.

With reference now to FIG. 4, the method may begin at 200. The base threshold is determined at 210. The humidity data 38 is evaluated at 220. If the humidity is within a predetermined range at 220, the humidity correction factor is determined based on the humidity data at 230. If, however, the humidity is outside of the predetermined range at 220, optionally, other correction factors are determined at 240 based on engine and/or exhaust system data 42. The correction factors are applied to the base threshold at 250 to determine the final threshold 44. Thereafter, the method may end at 260.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the application.

What is claimed is:

1. A method of monitoring a sensor of an exhaust system, comprising:
    evaluating humidity of air entering the exhaust system; and
    monitoring operation of a sensor in the exhaust system based on the humidity,
    wherein the evaluating comprises evaluating whether the humidity is within a predetermined range, and when the humidity is within the predetermined range, enabling the monitoring the operation of the sensor.

2. The method of claim 1, wherein the sensor is a NOx sensor.

3. The method of claim 1, wherein when the humidity is outside of the predetermined range, disabling the monitoring the operation of the sensor.

4. The method of claim 3, further comprising setting a value of a diagnostic code based on the monitoring.

5. A method of monitoring a sensor of an exhaust system, comprising:
    evaluating humidity of air entering the exhaust system;
    monitoring operation of a sensor in the exhaust system based on the humidity;
    determining a correction factor based on the humidity; and
    applying the correction factor to a threshold,
    wherein the monitoring the operation of the sensor is based on the threshold.

6. The method of claim 5, further comprising evaluating whether the humidity is within a predetermined range, and wherein when the humidity is within the predetermined range, enabling the determining the correction factor.

7. The method of claim 6, further comprising evaluating whether the humidity is within a predetermined range, and wherein when the humidity is outside the predetermined range, disabling the determining the correction factor.

8. A system for monitoring a sensor of an exhaust system, comprising:
- a first module that evaluates humidity of air entering the exhaust system; and
- a second module that monitors operation of a sensor in the exhaust system based on the humidity,
- wherein the first module evaluates whether the humidity is within a predetermined range, and when the humidity is within the predetermined range, the second module enables the monitoring the operation of the sensor.

9. The system of claim 8, wherein when the humidity is outside of the predetermined range, the second module disables the monitoring the operation of the sensor.

10. The system of claim 9, further comprising a third module that sets a value of a diagnostic code based on the monitoring and that generates a message including the diagnostic code.

11. A system for monitoring a sensor of an exhaust system, comprising:
- a first module that evaluates humidity of air entering the exhaust system;
- a second module that monitors operation of a sensor in the exhaust system based on the humidity; and
- a third module that determines a correction factor based on the humidity, and that applies the correction factor to a threshold,
- wherein the second module monitors the operation of the sensor based on the threshold.

12. The system of claim 11, wherein the sensor is a NOx sensor.

13. The system of claim 11, wherein the third module evaluates whether the humidity is within a predetermined range, and when the humidity is within the predetermined range, the third module determines the correction factor.

14. The system of claim 13, wherein the third module evaluates whether the humidity is within a predetermined range, and when the humidity is outside the predetermined range, the third module does not determine the correction factor.

* * * * *